(12) United States Patent
Hsieh (10) Patent No.: US 10,366,280 B2
(45) Date of Patent: Jul. 30, 2019

(54) METHOD AND APPARATUS FOR MEASURING PERIODIC MOTION

(71) Applicant: Mitac International Corp., Taoyuan (TW)

(72) Inventor: Hsiang-Yu Hsieh, Taoyuan (TW)

(73) Assignee: Mitac International Corp., Taoyuan (TW)

( * ) Notice: Subject to any disclaimer, the term of this patent is extended or adjusted under 35 U.S.C. 154(b) by 718 days.

(21) Appl. No.: 14/596,559

(22) Filed: Jan. 14, 2015

(65) Prior Publication Data

US 2015/0198462 A1    Jul. 16, 2015

(30) Foreign Application Priority Data

Jan. 15, 2014 (TW) .............................. 103101452 A (51) Int. Cl.
*G06K 9/00* (2006.01)
*G16H 20/30* (2018.01)
*A61B 5/11* (2006.01)

(52) U.S. Cl.
CPC ......... *G06K 9/00342* (2013.01); *G16H 20/30* (2018.01); *A61B 5/1114* (2013.01)

(58) Field of Classification Search
None
See application file for complete search history.

(56) References Cited

FOREIGN PATENT DOCUMENTS

TW    200538751 A    12/2005
TW    201226908 A    7/2012

OTHER PUBLICATIONS

Search Report appended to an Office Action issued to Taiwanese Counterpart Application No. 103101452 by the TIPO dated Apr. 7, 2015, with an English translation thereof.
Search Report appended to an Office Action issued to Chinese Counterpart Application No. 201410216624.7 by the SIPO dated Jun. 28, 2017, with an English translation thereof.

*Primary Examiner* — John E Breene
*Assistant Examiner* — Jeffrey C Morgan
(74) *Attorney, Agent, or Firm* — SmithAmundsen LLC (57) ABSTRACT

A method for measuring periodic motion of an object includes the steps of: after receiving an axial acceleration and a radial acceleration, calculating a first included angle between a composite acceleration, which is a sum of the axial acceleration and the radial acceleration, and one of an axial direction and a radial direction, and a second included angle between the composite acceleration and the other one of the axial direction and the radial direction; and based on a magnitude relation between the second included angle and the first included angle, controlling a periodic motion counter to increment a motion counter value which is associated with a number of times the periodic motion of the object has occurred.

19 Claims, 11 Drawing Sheets

METHOD AND APPARATUS FOR MEASURING PERIODIC MOTION

CROSS-REFERENCE TO RELATED APPLICATION

This application claims priority of Taiwanese Patent Application No. 103101452, filed on Jan. 15, 2014, the entire disclosure of which is incorporated herein by reference.

BACKGROUND OF THE INVENTION

1. Field of the Invention

The invention relates to measurement of motion, more particularly to a method and an apparatus for measuring periodic motion.

2. Description of the Related Art

Many current electronic products, such as a pedometer provided with an accelerometer or a mobile phone provided with the accelerometer in combination with a mobile phone application program, can count a number of steps a user takes. Alternatively, the accelerometer has been arranged on a watch for calculating swimming stroke count.

A conventional technique associated with the accelerometer is to perform signal analysis in the frequency domain, to design filters having a distinct threshold parameters. However, for different kinds of exercises relating to divergent body movements, such as swinging, shaking or rotating, a corresponding filter or algorithm is required to be redesigned for accurate measurement of the body movements. Moreover, some algorithms are required to be modified for setting threshold parameters in different situation. Therefore, how to design a counter suitable for use in different kinds of exercises has always been an important issue in the industry.

SUMMARY OF THE INVENTION

An object of the present invention is to provide a method adapted for measuring periodic motion and suitable for use in different types of periodic movements.

Accordingly, the method of the present invention is configured for measuring periodic motion of an object. The method is to be implemented by an apparatus that includes an accelerometer, a processor and a periodic motion counter. The accelerometer generates an axial acceleration that represents an axial component of an acceleration of the object in an axial direction and a radial acceleration that represents a radial component of the acceleration of the object in a radial direction orthogonal to the axial direction by detecting the motion of the object. The method includes the following steps, which are to be performed by the processer, of:

(A) receiving the axial acceleration and the radial acceleration generated by the accelerometer;

(B) calculating a first included angle between a composite acceleration and one of the axial direction and the radial direction, and a second included angle between the composite acceleration and the other one of the axial direction and the radial direction, wherein the composite acceleration is a sum of the axial component of acceleration and the radial component of acceleration; and (C) based on a magnitude relation between the second included angle and the first included angle, controlling the periodic motion counter to increment a motion counter value.

The magnitude relation is that a sign of a difference between the second included angle and the first included angle is reversed.

Another object of the present invention is to provide an apparatus adapted for measuring periodic motion and suitable for different types of periodic movements.

Accordingly, the apparatus of the present invention is configured for measuring periodic motion of an object. The apparatus includes an accelerometer, a processor coupled to the accelerometer, and a periodic motion counter coupled to the processor.

The accelerometer generates an axial acceleration that represents an axial component of an acceleration of the object in an axial direction and a radial acceleration that represents a radial component of the acceleration of the object in a radial direction perpendicular to the axial direction by detecting the motion of the object.

The processor, receives the axial acceleration and the radial acceleration generated by the accelerometer, calculates a first included angle between a composite acceleration and one of the axial direction and the radial direction, and a second included angle between the composite acceleration and the other one of the axial direction and the radial direction. The composite acceleration is a sum of the axial component of acceleration and the radial component of acceleration. The processor, based on a magnitude relation between the second included angle and the first included angle, controls the periodic motion counter to increment a motion counter value. The magnitude relation is that a sign of a difference between the second included angle and the first included angle is reversed.

An effect of the present invention resides in that, by calculating the first included angle between the composite acceleration and one of the axial direction and the radial direction, and the second included angle between the composite acceleration and the other one of the axial direction and the radial direction, and by determining the magnitude relation between the second included angle and the first included angle, the number of times the periodic motion has occurred may be measured regardless of the kind of periodic movement.

BRIEF DESCRIPTION OF THE DRAWINGS

Other features and advantages of the present invention will become apparent in the following detailed description of an embodiment with reference to the accompanying drawings, of which.

DETAILED DESCRIPTION OF THE EMBODIMENT

Figure 1:
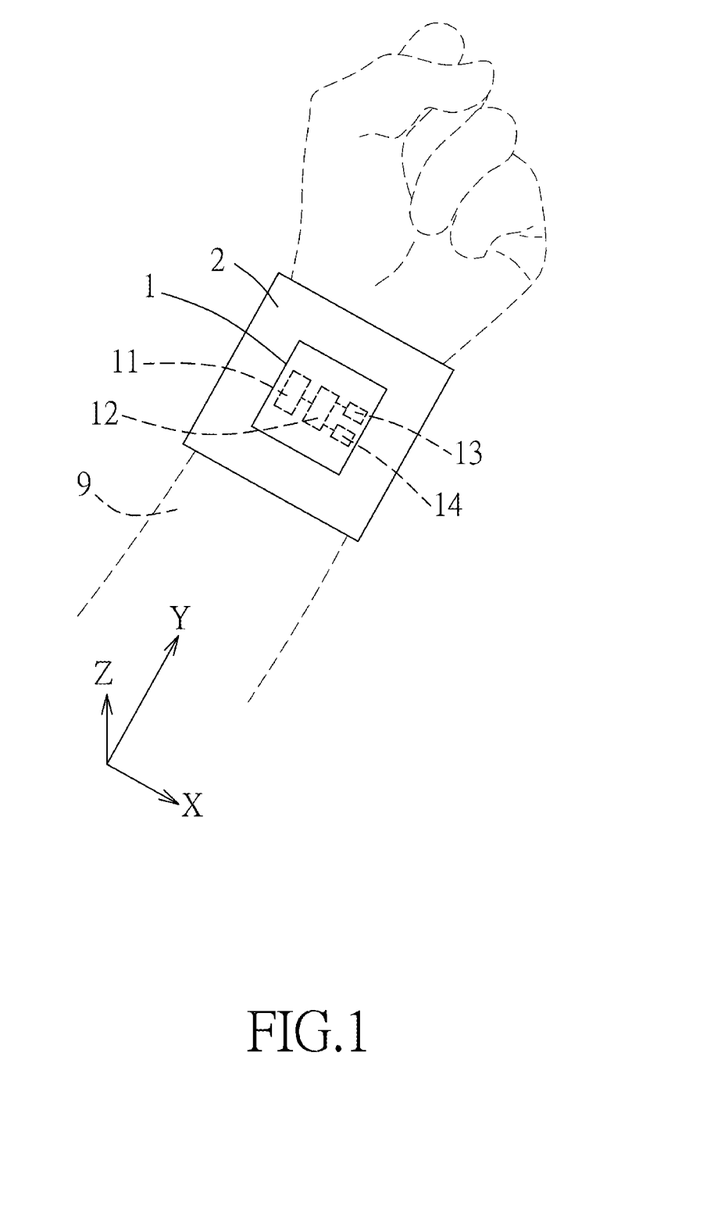
FIG. 1 is a schematic diagram illustrating an apparatus for implementing a method for measuring periodic motion according to the present invention.
Figure 2:
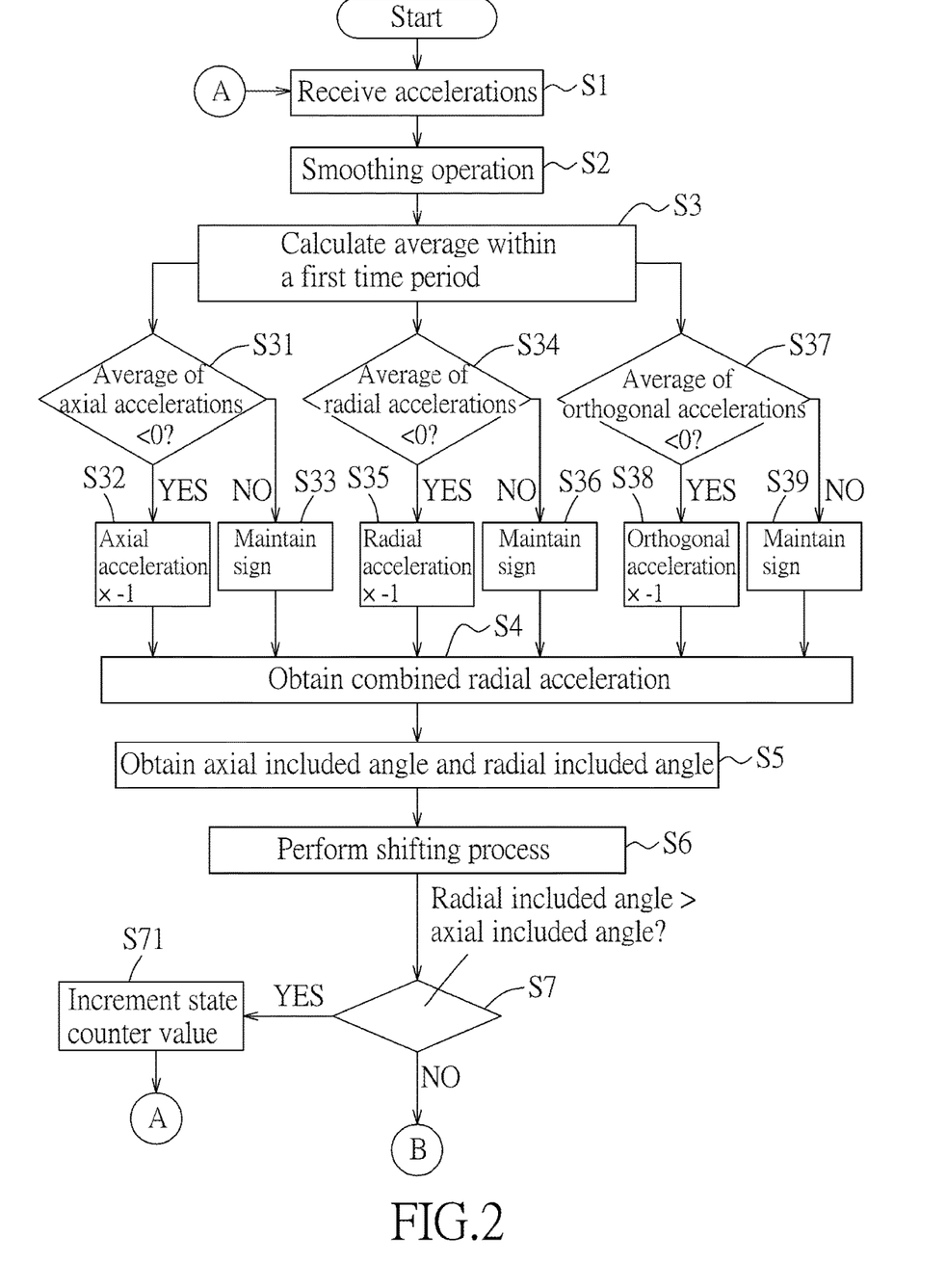
FIG. 2 is a flow chart illustrating an embodiment of the method according to the present invention.
Figure 3:
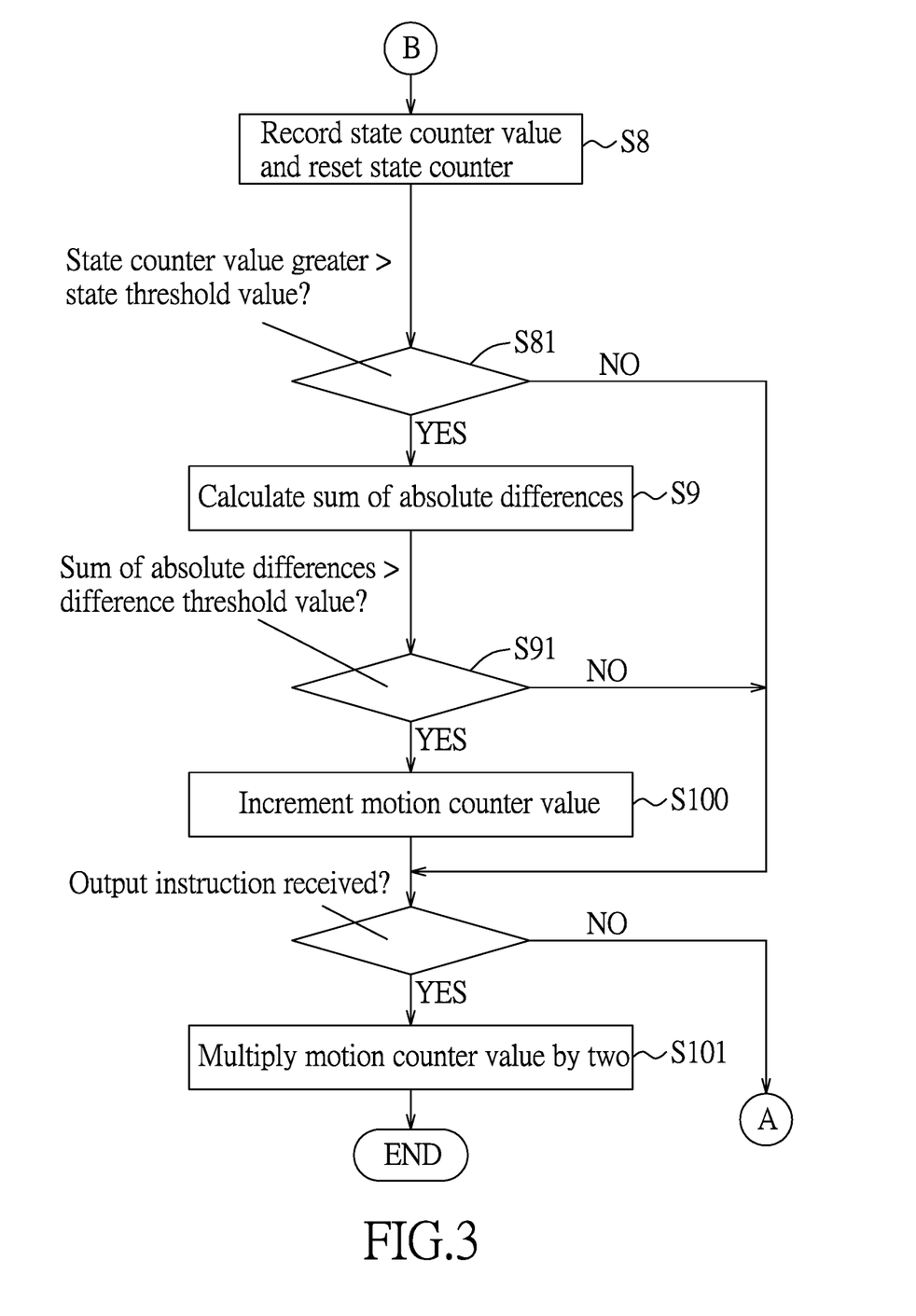
FIG. 3 is a flowchart illustrating the embodiment of the present invention.

Referring to FIG. 1 to FIG. 3, an embodiment of a method for measuring periodic motion of an object according to the present invention is illustrated. The method is to be implemented by an apparatus 1 for measuring periodic motion of the object. The apparatus 1 is arranged on a band unit 2 for attachment to the object. For example, the apparatus 1 together with the band unit 2 is to be worn by a user on a limb 9 of the user, such as an arm (see FIG. 1) or a leg (not shown). The band unit 2 is exemplified as a wrist brace or a knee brace. The apparatus 1 includes an accelerometer 11, a processor 12 coupled to the accelerometer 11, a periodic motion counter 13 coupled to the processor 12, and a state counter 14 coupled to the processor 12. The accelerometer 11 is exemplified as a three-axis accelerometer in this embodiment, but may be a two-axis accelerometer in other embodiments. The accelerometer of this embodiment is configured to detect components of an acceleration of the object in X, Y and Z axes, which are orthogonal. The apparatus 1 is worn in a manner that the Y axis is parallel to an axial direction of the limb 9. Directions of the X and Z axes may vary according to different uses of the apparatus 1. Hence, in this embodiment, the direction of the X axis is defined as a radial direction, and the direction of the Z axis is defined as an orthogonal direction. When the apparatus 1 is worn on the limb 9, the accelerometer 11, according to the periodic motion of the object, is configured to generate vector data of an axial acceleration that represents an axial component of the acceleration of the object in the axial direction, vector data of a radial acceleration that represents a radial component of the acceleration of the object in the radial direction perpendicular to the axial direction, and vector data of an orthogonal acceleration that represents a third component of the acceleration of the object in a third direction that is orthogonal to both the axial direction and the radial direction.

The embodiment of the method according to the present invention includes the following steps which the processor 12 is configured to perform.

In step S1, the processor 12 receives the generated accelerations, i.e., the axial acceleration, the radial acceleration and the orthogonal acceleration, generated by the accelerometer 11. In this embodiment, the accelerometer 11 generates 60 entries of the axial accelerations, 60 entries of the radial accelerations and 60 entries of the orthogonal accelerations every one second.

In step S2, a smoothing (filtering) operation is performed, i.e., each of the generated accelerations is smoothened. Specifically, for each of a latest one of the axial accelerations, a latest one of the radial accelerations and a latest one of the orthogonal accelerations received within a previous fifth time period, the processor 12 calculates an average of a respective one of the axial accelerations, the radial accelerations and the orthogonal accelerations within the previous fifth time period. The average thus calculated serves as a corresponding one of the axial acceleration, the radial acceleration and the orthogonal acceleration to be processed in the following steps. The purpose of this step is to filter out extreme values in the raw data, i.e., the generated accelerations, while maintaining characteristics of waveforms of the raw data. In this embodiment, the fifth time period is one-third of a second, that is to say, an average of 20 entries of each of the axial accelerations, the radial accelerations and the orthogonal accelerations is calculated in this step.

In step S3, the processor 12 calculates an average of each of the axial accelerations, the radial accelerations and the orthogonal accelerations received within a previous first time period. The purpose of this step is to find a main component of each of the generated accelerations, so as to determine whether each of the generated accelerations is mostly greater than zero or smaller than zero.

Figure 4:
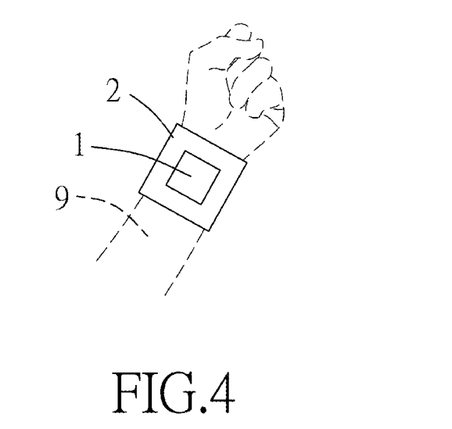
FIG. 4 is a schematic diagram illustrating that the apparatus is worn on an inner side of a wrist.
Figure 5:
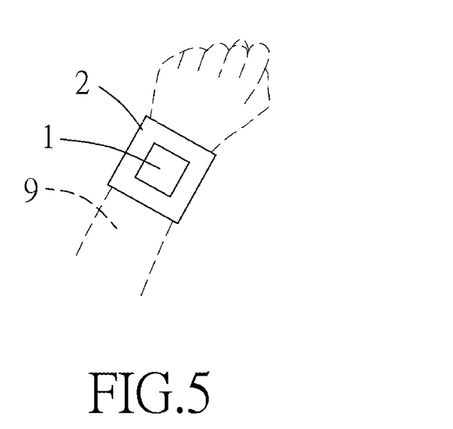
FIG. 5 is a schematic diagram illustrating that the apparatus is worn on an outer side of the wrist.
Figure 6:
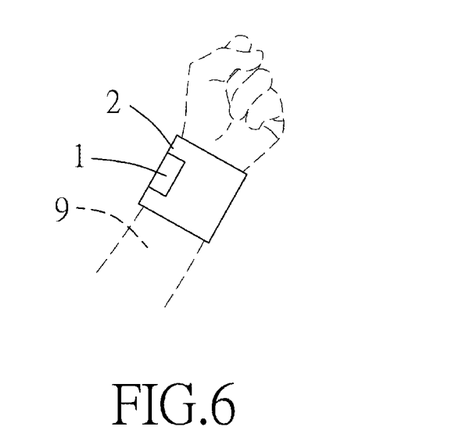
FIG. 6 is a schematic diagram illustrating that the apparatus is worn on one side of the wrist adjacent to a thumb.
Figure 7:
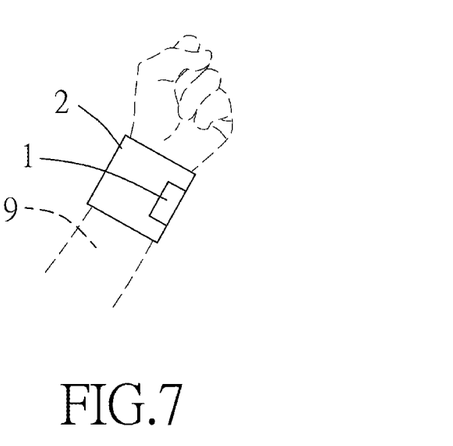
FIG. 7 is a schematic diagram illustrating that the apparatus is worn on another side of the wrist adjacent to a little finger.
Figure 8:
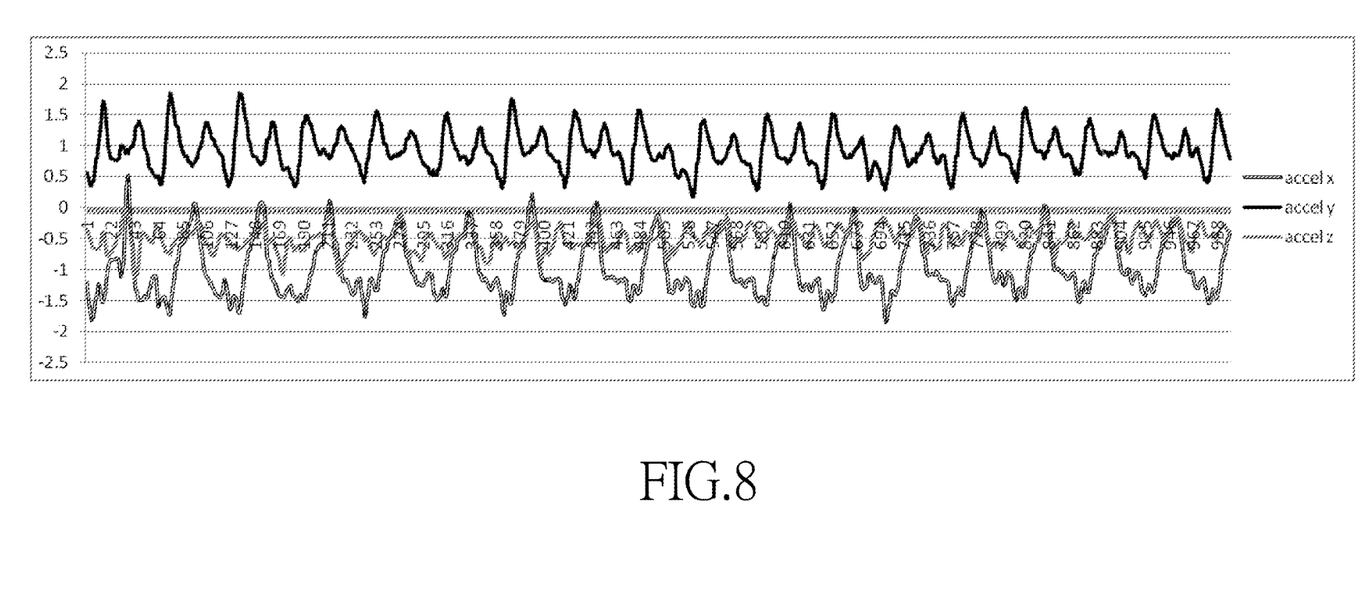
FIG. 8 illustrates radial accelerations, axial accelerations, and orthogonal accelerations.

As mentioned above, different users may have different use of the apparatus 1, for example, the apparatus 1 may be worn on an inner side of a wrist (see FIG. 4), on an outer side of the wrist (see FIG. 5), on one side of the wrist adjacent to a thumb (see FIG. 6), or on another side of the wrist adjacent to a little finger (see FIG. 7). Therefore, the main component of each of the generated accelerations may diverge, which may be evident as FIG. 8. Referring to FIG. 8, the main component of the axial accelerations (accel y) is greater than zero, whereas the main components of the radial accelerations (accel x) and the orthogonal accelerations (accel z) are smaller than zero. The purpose of finding the main components will be explained in the following paragraphs.

In this embodiment, the first time period is 5 seconds, that is to say the average of 300 entries of each of the axial accelerations, the radial accelerations and the orthogonal accelerations is calculated in this step.

The following steps S31 to S33 are performed for a latest one of the axial accelerations received within the previous first time period. Specifically, the processor 12 inputs the axial acceleration to a reverse process which includes sub-steps S31 to S33.

In step S31, the processor 12 determines whether the average of the axial accelerations thus calculated satisfies an inequality that the average is smaller than zero.

In step S32, the processor 12 generates a sign-processed axial acceleration by multiplying the latest one of the axial accelerations by minus one if the inequality is satisfied.

In step S33, the processor 12 generates the sign-processed axial acceleration by maintaining a sign of the latest one of the axial accelerations if the inequality is not satisfied.

The following steps S34 to S36 are performed for a latest one of the radial accelerations received within the previous first time period. Specifically, the processor 12 inputs the radial acceleration to a reverse process which includes sub-steps S33 to S36.

In step S34, the processor 12 determines whether the average of the radial accelerations thus calculated satisfies an inequality that the average is smaller than zero.

In step S35, the processor 12 generates a sign-processed radial acceleration by multiplying the latest one of the radial accelerations by minus one if the inequality is satisfied.

In step S36, the processor 12 generates the sign-processed radial acceleration by maintaining a sign of the latest one of the radial accelerations if the inequality is not satisfied.

The following steps S37 to S39 are performed for a latest one of the orthogonal accelerations received within the previous first time period. Specifically, the processor 12 inputs the orthogonal acceleration to a reverse process which includes sub-steps S37 to S39.

In step S37, the processor 12 determines whether the average of the orthogonal accelerations thus calculated satisfies an inequality that the average is smaller than zero.

In step S38, the processor 12 generates a sign-processed orthogonal acceleration by multiplying the latest one of the orthogonal accelerations by minus one if the inequality is satisfied.

In step S39, the processor 12 generates the sign-processed orthogonal acceleration by maintaining a sign of the latest one of the orthogonal accelerations if the inequality is not satisfied.

It should be noted that, in this embodiment, the latest one of the corresponding generated accelerations received within the previous first time period is multiplied by minus one if the respective average thus calculated is smaller than zero, such that the main component of each of the generated accelerations may be greater than zero. However, the practical implementation is not limited to the disclosure herein, and alternatively, the corresponding acceleration may be multiplied by minus one if the average is greater than zero such that the main component of each of the generated accelerations may be smaller than zero.

In step S4, the processor 12 calculates a combined radial acceleration by subjecting the sign-processed radial acceleration and the sign-processed orthogonal acceleration to an addition equation, in which a magnitude of the combined radial acceleration equals a magnitude of the sign-processed radial acceleration plus a magnitude of the sign-processed orthogonal acceleration. The combined radial acceleration represents a combination of the another component of the acceleration of the object in the radial direction and the third component of the acceleration of the object in the orthogonal direction. This step may be omitted in an embodiment where the two-axis accelerometer is adopted. Moreover, the addition equation is exemplified by scalar addition in this embodiment for saving computational load, but may also be exemplified by vector addition, i.e., a square root of the sum of squares of two entries of vectors. However, which kind of addition equation is adopted does not affect subsequent determinations. This will be explained hereinbelow.

Figure 9:
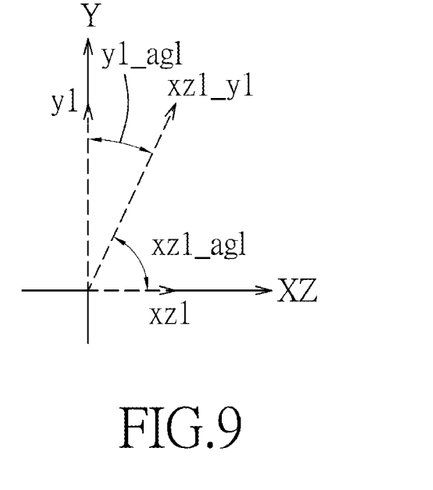
FIG. 9 illustrates that a composite acceleration is located at the first quadrant of a Cartesian coordinate system.

Referring to FIG. 9, the combined radial acceleration is denoted as a vector xz1 that is located on a virtual XZ axis, and the axial acceleration is denoted as a vector y1 that is located on the Y axis. These vectors are plotted on a Cartesian coordinate system defined by the XZ axis and the Y axis of FIG. 9. Since the addition equation of step S4 is exemplified by the scalar addition in this embodiment, the virtual XZ axis in fact does not correspond to any direction in a three-dimensional space. However, because the radial acceleration and the orthogonal acceleration are both perpendicular to the axial acceleration, it is reasonable to define the XZ axis to be perpendicular to the Y axis. Accordingly, a composite acceleration xz1_y1 may be defined as a sum (e.g., vector sum) of the vector xz1 (i.e., the combined radial acceleration) and the vector y1 (i.e., the axial acceleration).

Figure 10:
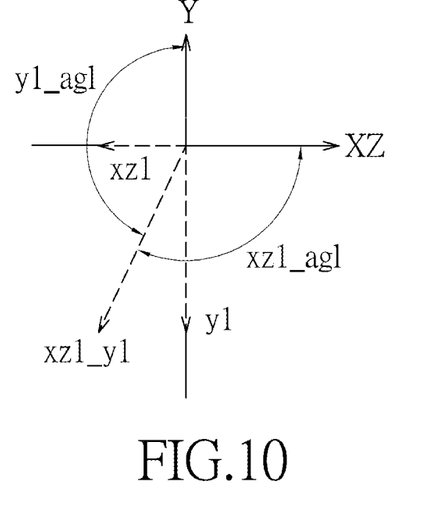
FIG. 10 illustrates that a composite acceleration is located at the third quadrant of the Cartesian coordinate system.
Figure 11:
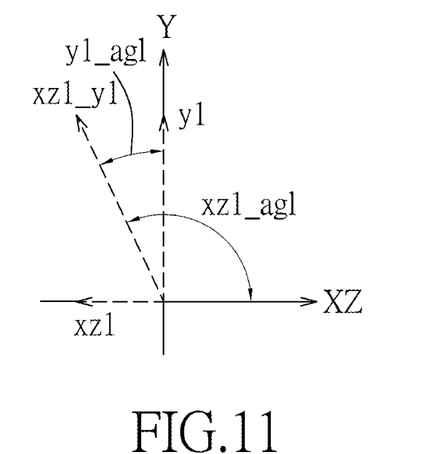
FIG. 11 illustrates that a composite acceleration is located at the second quadrant of the Cartesian coordinate system.
Figure 12:
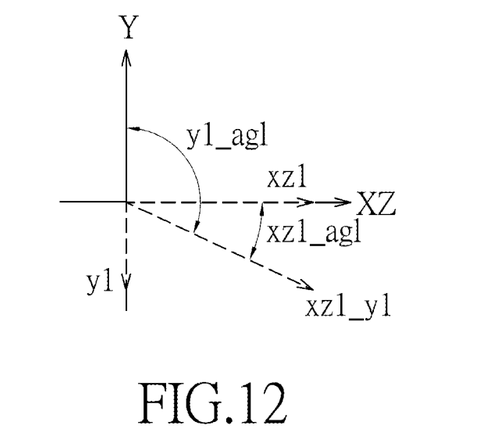
FIG. 12 illustrates that a composite acceleration is located at the fourth quadrant of the Cartesian coordinate system.

In the present invention, the periodic motion of the object can be measured based on a magnitude relation between a first included angle y1_agl and a second included angle xz1_agl. The first included angle y1_agl is between the composite acceleration xz1_y1 and the Y axis (i.e., the axial direction, hence referred to as an axial included angle hereinafter). The second included angle xz1_agl is between the composite acceleration xz1_y1 and the XZ axis (referred to as radial included angle hereinafter). Specifically, the magnitude relation is that a sign of a difference between the second included angle xz1_agl and the first included angle y1_agl is reversed, such as changed from positive to negative, or changed from negative to positive. Depend on a sign of each of the vector xz1 and the vector y1, the composite acceleration xz1_y1 may be located at one of four possible quadrants. When the composite acceleration xz1_y1 is located at the first quadrant (see FIG. 9) or the third quadrant (see FIG. 10) of the Cartesian coordinate system, the axial included angle y1_agl is observed as increasing while the radial included angle zx1_agl is decreasing, and in contrast, the axial included angle y1_agl is observed as decreasing while the radial included angle zx1_agl is increasing. When the composite acceleration xz1_y1 is located at the second quadrant (see FIG. 11) or the fourth quadrant (see FIG. 12) of the Cartesian coordinate system, the axial included angle y1_agl and the radial included angle zx1_agl are increasing simultaneously or decreasing simultaneously.

Figure 13:
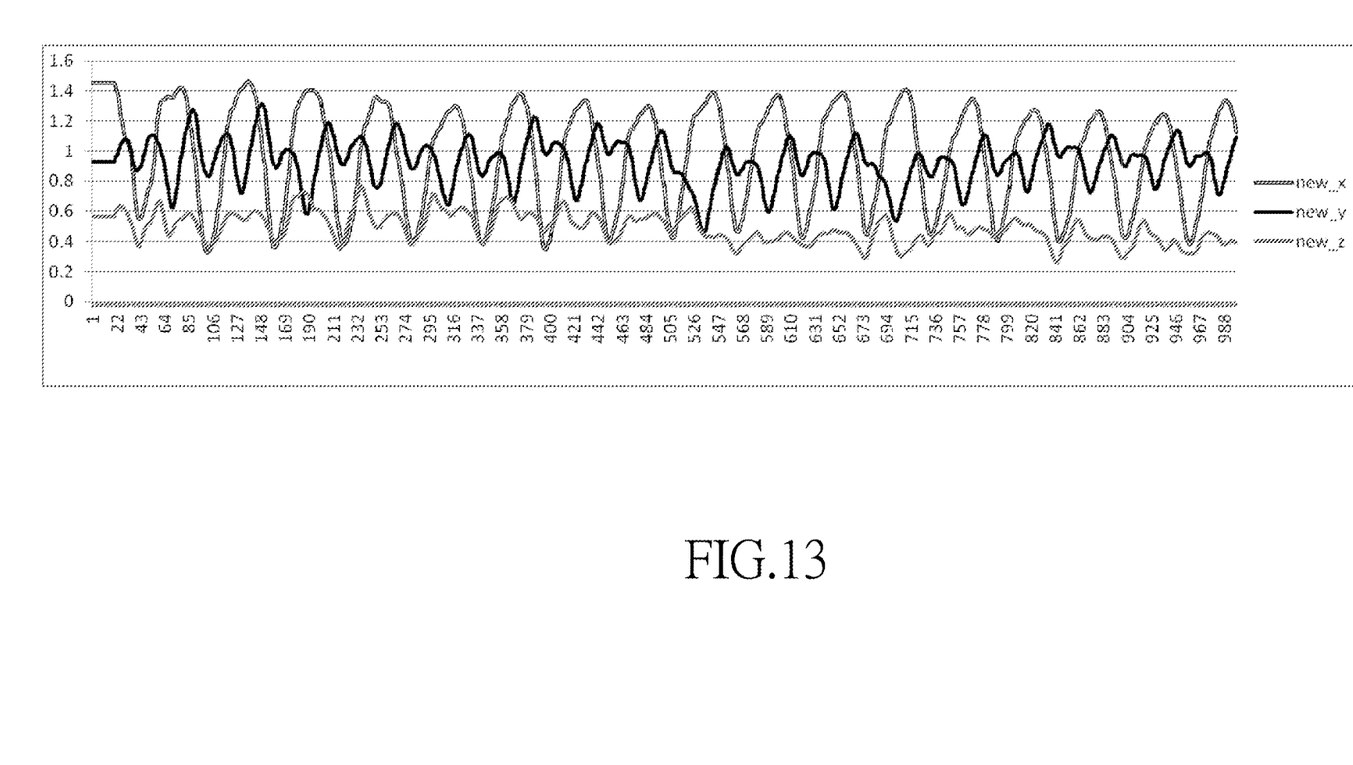
FIG. 13 illustrates sign-processed radial accelerations, sign-processed axial accelerations, and sign-processed orthogonal accelerations.
Figure 14:
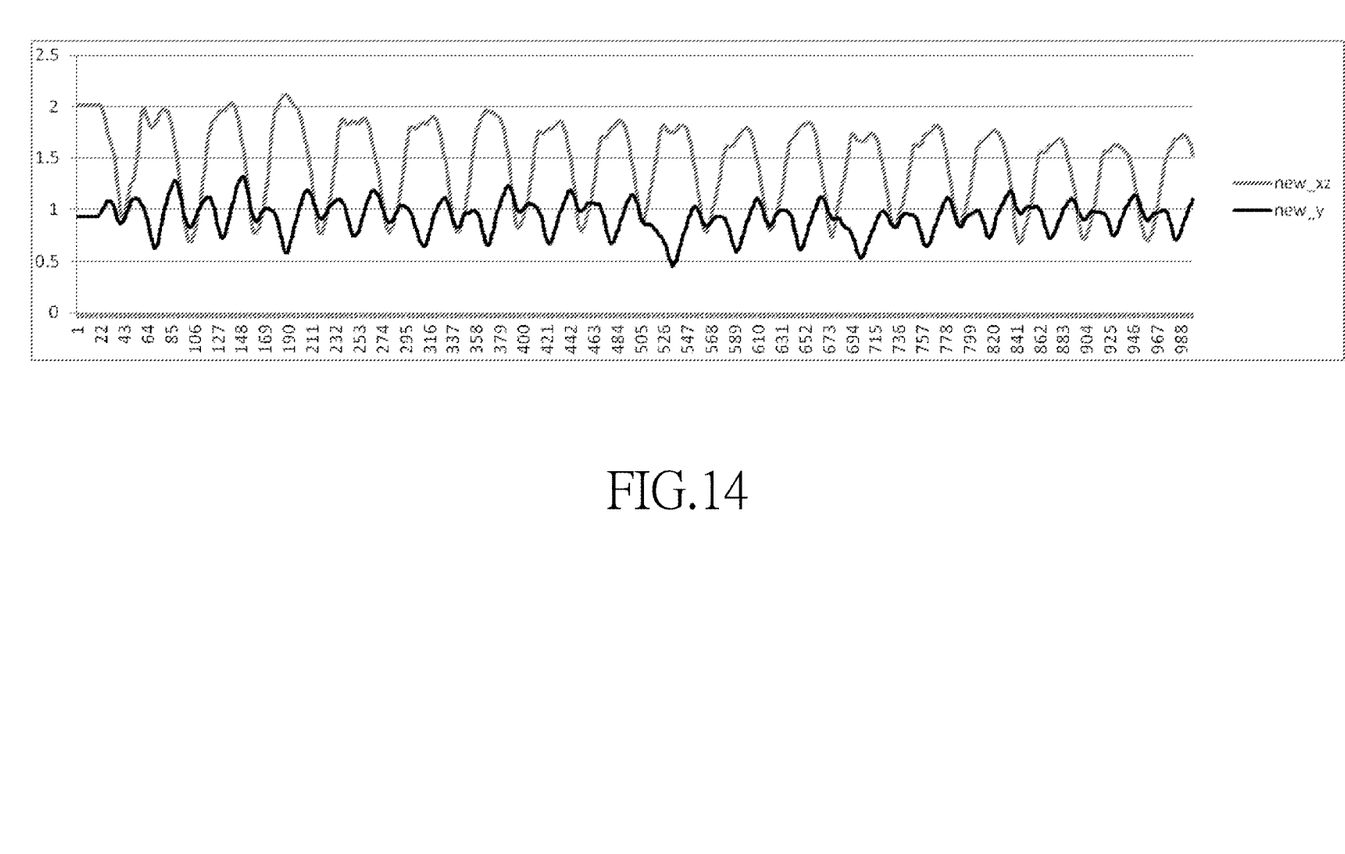
FIG. 14 illustrates the sign-processed axial accelerations and combined radial accelerations.

In order to measure the periodic motion of the object based on the magnitude relation between the radial included angle xz1_agl and the axial included angle y1_agl (e.g., one is increasing while the other one is decreasing), the composite acceleration xz1_y1 is preferably located at one of the first quadrant and the third quadrant. In this embodiment, the first quadrant is selected for subsequent analysis. In order to ensure that the composite acceleration xz1_y1 is located at the first quadrant, the aforementioned step S3 associated with finding the main component, and steps S31 to S39 associated with sign processing are thus performed, so as to enable the sign-processed accelerations in three directions to be mostly greater than zero (see FIG. 13). The combined radial acceleration calculated via the addition equation is also greater than zero (see FIG. 14, the waveform on the top side denotes the combined radial acceleration while the waveform on the bottom side denotes the sign-processed axial acceleration). Moreover, because the periodic motion is measured based on the magnitude relation between two angles, whether the scalar addition or the vector addition is adopted for calculating the combined radial acceleration (i.e., the vector xz_1) is a viable option.

Alternatively, when the two-axis accelerometer is adopted to serve as the accelerometer 11, two accelerations generated in two axes may be used to calculate the two included angles directly. However, when the object is moving in a direction which is not detected by the two-axis accelerometer, mismeasurements may occur.

Referring to FIG. 2 and FIG. 9, in step S5, the processor 12 calculates the axial included angle y1_agl between the composite acceleration xz1_y1 and the axial direction (vector y1), and the radial included angle xz1_agl between the composite acceleration xz1_y1 and the radial direction (vector xz1). According to trigonometric functions, in a first approach, a magnitude (L_xz_y) of the composite acceleration xz1_y1 is first calculated by calculating the square root of the sum of squares of a magnitude (new_xz) of the combined radial acceleration and a magnitude (new_y) of the sign-processed axial acceleration, which can be expressed as:

$$L\_xz\_y=\text{sqrt}((\text{new}\_xz)^2+(\text{new}\_y)^2).$$

Subsequently, the following arccosine functions are calculated:

$$y1\_agl=\arccos(\text{new}\_y/L\_xz\_y); \text{ and}$$

$$xz1\_agl=\arccos(\text{new}\_xz/L\_xz\_y).$$

Alternatively, in a second approach, the following arctangent functions may be calculated:

$$y1\_agl=\arctan(\text{new}\_xz/\text{new}\_y); \text{ and}$$

$$xz1\_agl=\arctan(\text{new}\_y/\text{new}\_xz).$$

Figure 15:
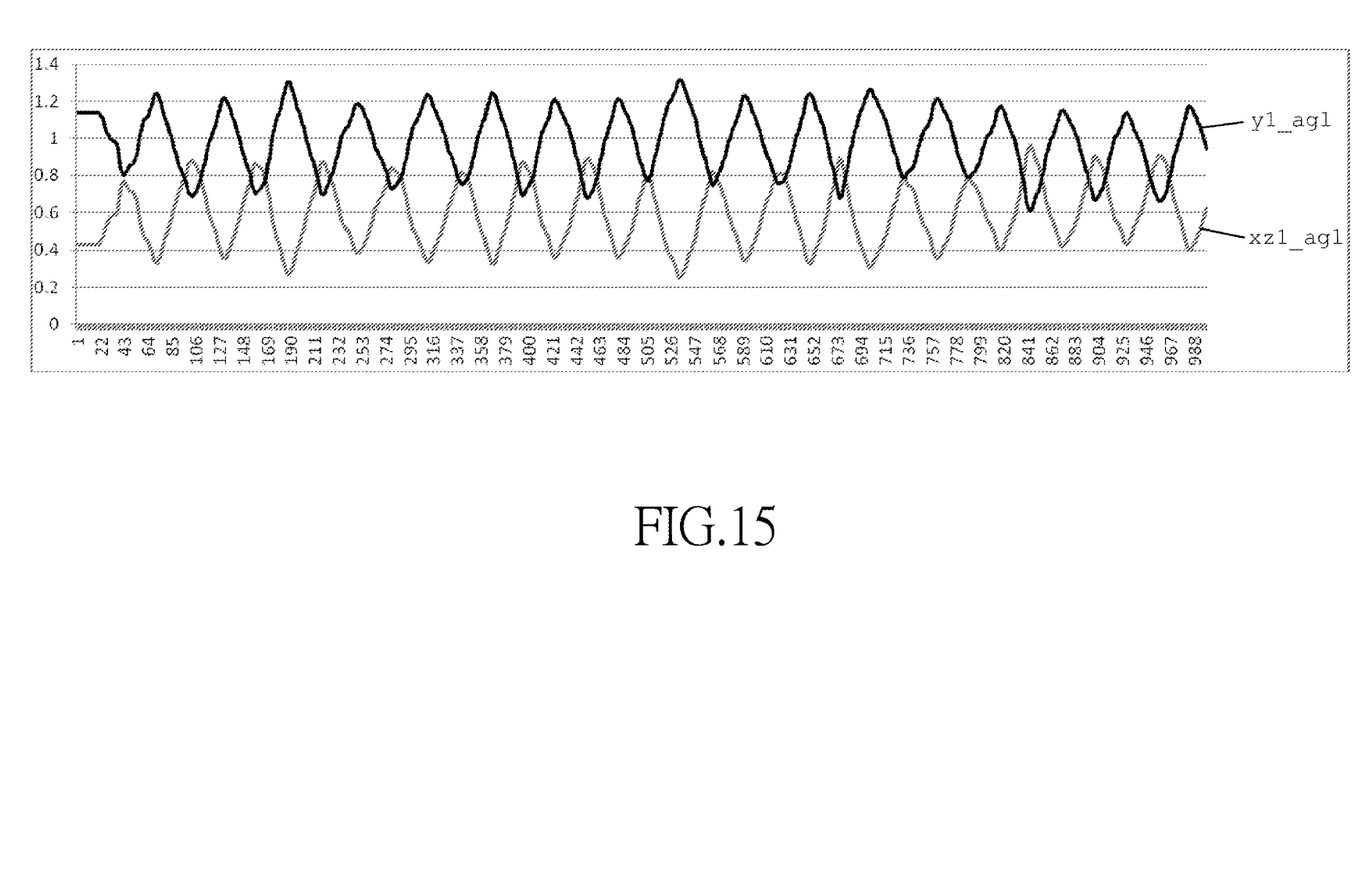
FIG. 15 illustrates axial included angles and radial included angles.

The axial included angle y1_agl and the radial included angle xz1_agl thus calculated are illustrated in FIG. 15. It is evident in FIG. 15 that one waveform may correspond to greater values and may be located upper the other waveform. The waveform on the upper side denotes the axial included angle y1_agl, and the waveform on the lower side denotes the radial included angle xz1_agl.

Figure 16:
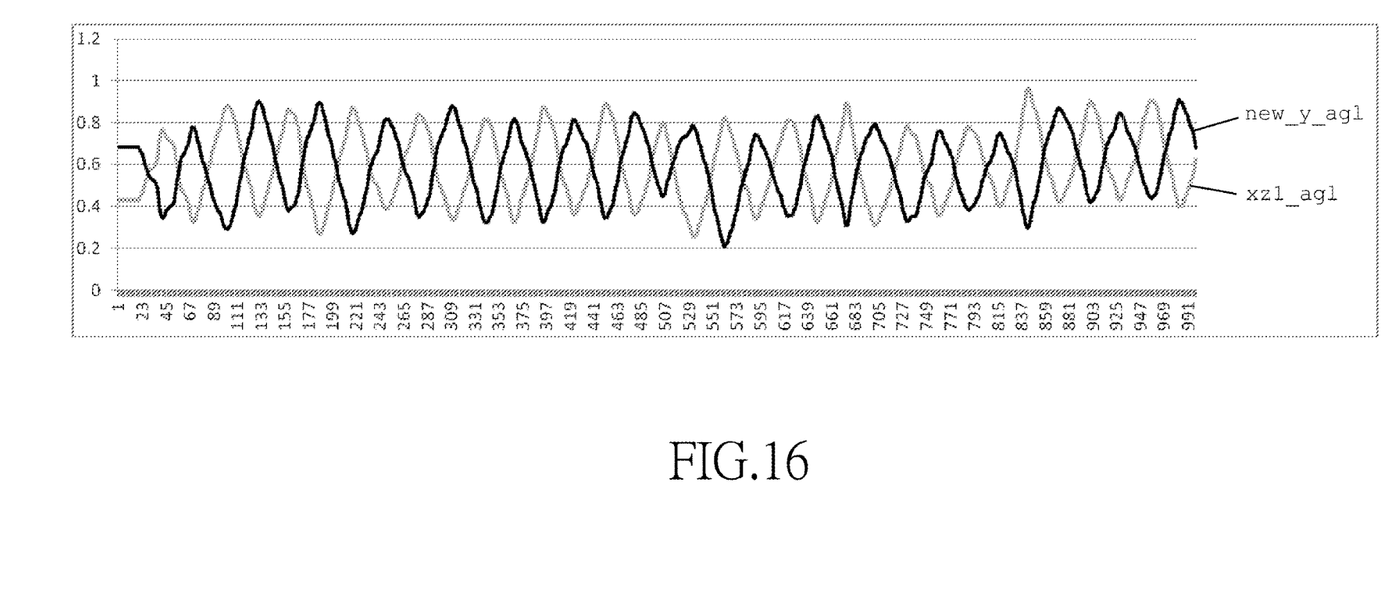
FIG. 16 illustrates shifted axial included angles and the radial included angles.

Referring to FIG. 2 and FIG. 16, in step S6, the processor 12 performs a shifting process. It is noted that in step S5, the processor 12 calculates a plurality of the axial included angles and a plurality of the radial included angles within a previous second time period based on the sign-processed axial accelerations and the combined radial accelerations. In the shifting process, the processor 12 first calculates a first average of the axial included angles y1_agl calculated thereby within the previous second time period, and a second average of the radial included angles xz1_agl calculated thereby within the previous second time period. In this embodiment, the second time period is one second, i.e., 60 entries of the axial included angles y1_agl and 60 entries of the radial included angles xz1_agl are processed. The second time period is selected for the purpose of representing the variation in the periodic motion of the object. The processor 12 then calculates a difference by subtracting the first average from the second average, i.e., $$\text{offset}=xz\_agl\_\text{avg}-y\_agl\_\text{avg},$$

wherein, offset denotes the difference, xz_agl_avg denotes the second average of the radial included angles xz1_agl, and y_agl_avg denotes the first average of the axial included angles y1_agl.

The processor 12 subsequently calculates a shifted axial included angle by adding the difference to a latest one of the axial included angles y1_agl calculated within the previous second time period, so as to shift the two included angles to the same basis, i.e., $$\text{new}\_y\_agl=y1\_agl+\text{offset},$$

wherein, new_y_agl denotes the shifted axial included angle. In this embodiment, the axial included angle y1_agl is shifted. However, the shifting process is not limited to the disclosure herein, and may be implemented by shifting the radial included angle xz1_agl in a variation of the embodiment. The shifted axial included angle is illustrated in FIG. 16.

In step S7, the processor 12 determines whether the radial included angle is greater than the axial included angle.

In step S71, the processor 12 controls the state counter 14 to increment a state counter value if the radial included angle is determined to be greater than the axial included angle in step S7, and the flow goes back to step S1.

Figure 17:
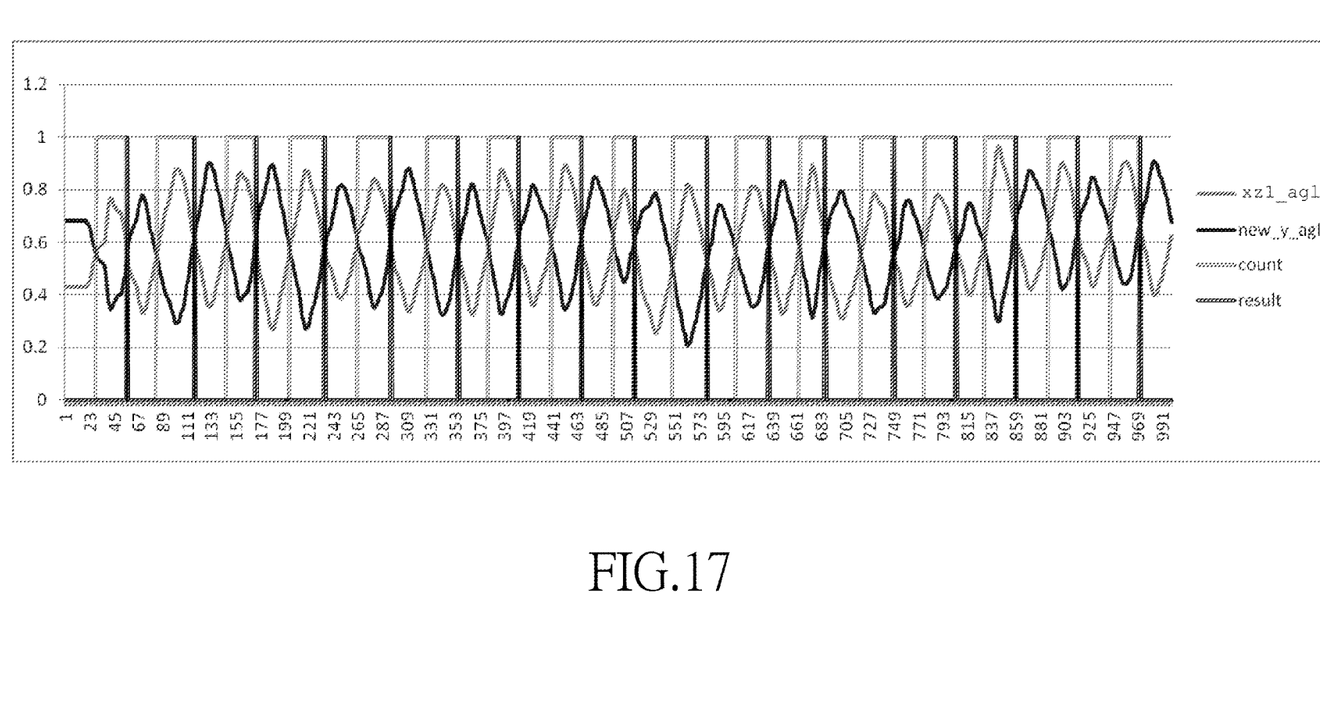
FIG. 17 illustrates time points at which a state counter and a periodic motion counter are controlled to increment.

Referring to FIG. 3 and FIG. 17, in step S8, if the radial included angle is determined to be not greater than the axial included angle in step S7, the processor 12 records the state counter value kept by the state counter 14, and resets the state counter 14 to zero. Specifically, the processor 12 records a plurality of the state counter values within a previous third time period, and calculates a state threshold value by multiplying an average of the state counter values recorded within the previous third time period by a factor that ranges between 0 and 1. In this embodiment, the third time period is selected to be equal to the first time period, i.e., 5 seconds, that is to say 300 entries of the state counter values are processed. The factor is exemplified to be 0.5.

The significance of this step is to find what the state counter value should be when the apparatus 1 detects a real periodic motion. An approach of this step is to first calculate the average of 300 entries of the state counter values within the previous third time period, and then to determine an reasonable state counter value by multiplying the average of the state counter values by 0.5. However, the step is not limited to the approach herein. The higher value of the factor stands for a stricter threshold being adopted. Otherwise, a more tolerant threshold is adopted.

In step S81, the processor 12 determines whether the state counter value recorded by the processor 12 in step S8 is greater than the state threshold value. The flow proceeds to step S101 if the state counter value recorded by the processor 12 is not greater than a state threshold value. And then, step S9 is performed.

In step S9, if the state counter value recorded by the processor 12 is greater than the state threshold value, the processor 12 calculates an absolute difference between each set of the shifted axial included angle new_y_agl and the radial included angle xz1_agl, i.e., $$\text{diff}\_xy\_y\_agl=\text{abs}(\text{new}\_y\_agl-xz1\_agl),$$

wherein diff_xy_y_agl denotes the absolute difference.

Subsequently, the processor 12 calculates a sum of the absolute differences calculated within a previous fourth time period. In this embodiment, the fourth time period is one-sixth of a second, i.e., 10 entries of data are processed.

In step S91, the processor 12 determines whether the sum of the absolute differences calculated within the previous fourth time period is greater than a predefined difference threshold value. The flow proceeds to step S101 if the sum of the absolute differences calculated within the previous fourth time period is not greater than the difference threshold value. Otherwise, step S100 is performed. The difference threshold value may be adjusted according to practical states of the apparatus 1, and may be defined in advance without requiring change due to different kinds of exercises.

The significance of steps S9 and S91 is to determine whether magnitudes of the shifted axial included angle and the radial included angle are too close. When the magnitudes of these two included angles are too close, it is possible that noise is involved during measurement of the periodic motion of the object. In this way, mismeasurement resulting from noise may be detected.

In step S100, if the sum of the absolute differences calculated within the previous fourth time period is greater than the predefined difference threshold value, the processor 12 controls the periodic motion counter 13 to increment a motion counter value which is kept by the motion counter 13, and which is associated with a number of times the periodic motion of the object has occurred. Results of this step are illustrated in FIG. 17. In FIG. 17, a waveform "count" shows time points at which the state counter 14 is controlled to increment the state counter value in step S71, and a waveform "result" shows time points at which the periodic motion counter 13 is controlled to increment the motion counter value in step S100.

In step S101, the processor 12 is configured to multiply the motion counter value that is kept by the periodic motion counter 13 by two to serve as the number of times the periodic motion of the object has occurred. The processor 12 may multiply the motion counter value by two and output the motion counter value thus multiplied when receiving an output instruction to provide the measured result.

In general, if the sum of the absolute differences calculated within the previous fourth time period is not greater than the predefined difference threshold value, for exercise relating to periodic motion, such as hiking and running, two steps are usually taken during a complete cycle of a periodic motion. Even for some swimming strokes, such as the front crawl or the backstroke, two arm strokes are taken during the complete cycle of periodic motion. As to other swimming strokes, such as the breaststroke and the butterfly stroke, the apparatus 1 may be set to refrain from multiplying the motion counter value kept by the periodic motion counter 13 by two. In this embodiment, the output instruction refers to an instruction inputted by the user to stop counting the periodic motion. However, the output instruction is not limited to the disclosure herein, and the apparatus 1 may output the result every time the periodic motion counter 13 increments, or alternatively may output the result each time the measuring processing has been conducted. The flow goes back to step S1 in the absence of a stop instruction.

To sum up, the processor 12 calculates the axial included angle between the composite acceleration and the axial direction, and the radial included angle between the composite acceleration and the radial direction. The processor 12 further processes the sign of each of the generated accelerations, and performs the shifting process so as to actuate measurement of the periodic motion. Moreover, the processor 12 further detects whether mismeasurement resulting from noise has occurred so as to promote accuracy of the measured result. The method of the present invention is also suitable for different kinds of exercises.

While the present invention has been described in connection with what is considered the most practical embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for measuring periodic motion of an object, the method to be implemented by an apparatus that includes an accelerometer which is attached to the object and oriented relative to the object so that a y-axis of the accelerometer is parallel to an axial direction of the object and an x-axis of the accelerometer is parallel to a radial direction of the object, a processor, a state counter, and a periodic motion counter, the method comprising the following steps, which are to be performed by the accelerometer and the processor, of:

(A) detecting, by the accelerometer, a periodic motion of the object so as to generate an axial acceleration along a y-axis that represents an axial component of an acceleration of the object in an axial direction and a radial acceleration along an x-axis that represents a radial component of the acceleration of the object in a radial direction, and receiving, by the processor, the axial acceleration and the radial acceleration generated by the accelerometer;

(B) calculating a first included angle between a composite acceleration and one of the axial direction and the radial direction, and a second included angle between the composite acceleration and the other one of the axial direction and the radial direction; wherein the composite acceleration is a sum of the axial component of acceleration and the radial component of acceleration;

(C) controlling the state counter to increment a state counter value if the second included angle is greater than the first included angle;

(D) if the second included angle is not greater than the first included angle, recording the state counter value kept by the state counter and resetting the state counter to zero;

(E) if the state counter value recorded in step (D) is greater than a state threshold value, controlling the periodic motion counter to increment a motion counter value kept by the periodic motion counter; wherein the motion counter value is associated with a number of times the periodic motion of the object has occurred; and (F) outputting the number of times the periodic motion of the object has occurred based on the motion counter value kept by the periodic motion counter;

whereby the periodic motion of the object may be measured regardless of the kind of periodic motion, including divergent movements of the object, including swinging, shaking, and rotating, and regardless of the orientation of the x-axis of the accelerometer about its v-axis.

2. The method according to claim 1, prior to step (B), further comprising the following steps, which are to be performed by the processor, of:

inputting the axial acceleration and the radial acceleration respectively to the reverse process;

generating a sign-processed axial acceleration and a sign-processed radial acceleration, respectively based on results of the reverse process;

wherein the axial acceleration and the radial acceleration respectively serve as an input acceleration to the inverse process, and the reverse process includes:

calculating an average of a plural entries of the input accelerations received within a previous first time period; and multiplying a latest one of the plural entries of the input accelerations by minus one if the inequality is satisfied by the average thus calculated;

wherein the inequality is one of the average is greater than zero and the average is smaller than zero; and wherein the sign-processed axial acceleration and the sign-processed radial acceleration correspond to the axial acceleration and the radial acceleration for calculating the first included angle and the second included angle in step (B).

3. The method according to claim 2, the accelerometer further generating an orthogonal acceleration that represents a third component of the acceleration of the object in another direction that is orthogonal to both the axial direction and the radial direction, the method further comprising the following steps, which are to be performed by the processor, of:

receiving the orthogonal acceleration generated by the accelerometer;

inputting the orthogonal acceleration to the reverse process;

generating a sign-processed orthogonal acceleration based on a result of the reverse process, the orthogonal acceleration serving as the input acceleration to the reverse process; and calculating a combined radial acceleration by subjecting the sign-processed radial acceleration and the sign-processed orthogonal acceleration to an addition equation, the combined radial acceleration thus calculated serving as the radial acceleration for calculating the first included angle and the second included angle.

4. The method according to claim 3, wherein, in the step of calculating the combined radial acceleration, a magnitude of the combined radial acceleration equals a magnitude of the sign-processed radial acceleration plus a magnitude of the sign-processed orthogonal acceleration.

5. The method according to claim 1, the accelerometer generating plural entries of the axial accelerations and plural entries of the radial accelerations within a previous second time period;

wherein, in step (B), the processor calculates a plurality of the first included angles and a plurality of the second included angles within the previous second time period based on the axial accelerations and the radial accelerations; and wherein the method further comprises, between step (B) and step (E), the step, which is to be performed by the processor, of:

performing a shifting process which includes:
calculating a first average of the first included angles and a second average of the second included angles;
calculating a difference between the first average from and the second average; and
calculating a shifted first included angle by adding the difference to a latest one of the first included angles calculated within the previous second time period.

6. The method according to claim 1, the accelerometer generating plural entries of the axial accelerations and plural entries of the radial accelerations within a previous third time period;

wherein, in step (D), the processor records a plurality of the state counter values within the previous third time period; and wherein, in step (E), the state threshold value is calculated by multiplying an average of the state counter values recorded in step (D) by a factor that ranges between 0 and 1.

7. The method according to claim 1, the accelerometer generating plural entries of the axial accelerations and plural entries of the radial accelerations within a previous fourth time period;

wherein, in step (B), the processor calculates a plurality of the first included angles and a plurality of the second included angles within the previous fourth time period based on the axial accelerations and the radial accelerations;

wherein the method further comprises, between steps (B) and (E), the following steps, which are to be performed by the processor, of:

calculating an absolute difference between each set of the first included angle and the second included angle; and proceeding to step (E), in which the periodic motion counter increments the motion counter value, if a sum of the absolute differences calculated within the previous fourth time period is greater than a difference threshold value.

8. The method according to claim 1, the accelerometer generating plural entries of the axial accelerations and plural entries of the radial accelerations within a previous fifth time period, the method, between steps (A) and (B), further comprising the following step, which is to be performed by the processor, of:

inputting each of a latest one of the axial accelerations and a latest one of the radial accelerations received within the previous fifth time period to a smoothing process;

wherein the smoothing process includes calculating an average of a respective one of the axial accelerations and the radial accelerations within the previous fifth time period, the average thus calculated serving as a corresponding one of the axial acceleration and the radial acceleration for calculating the first included angle and the second included angle.

9. The method according to claim 1, wherein step (F) includes:

multiplying the motion counter value by two to serve as the number of times the periodic motion of the object has occurred.

10. An apparatus for measuring periodic motion of an object, the apparatus comprising an accelerometer which is attached to the object and oriented relative to the object so that a y-axis of the accelerometer is parallel to an axial direction of the object and an x-axis of the accelerometer is parallel to a radial direction of the object, a processor coupled to said accelerometer, a state counter, and a periodic motion counter coupled to said processor;

wherein said accelerometer is configured to detect a periodic motion and generate an axial acceleration along a y-axis that represents an axial component of an acceleration of the object in an axial direction and a radial acceleration along an x-axis that represents a radial component of the acceleration of the object in a radial direction; and wherein said processor:

receives the axial acceleration and the radial acceleration generated by the accelerometer;

calculates a first included angle between a composite acceleration and one of the axial direction and the radial direction, and a second included angle between the composite acceleration and the other one of the axial direction and the radial direction, wherein the composite acceleration is a sum of the axial component of acceleration and the radial component of acceleration;

controls said state counter to increment a state counter value if the second included angle is greater than the first included angle;

if the second included angle is not greater than the first included angle, records the state counter value kept by said state counter, and resets said state counter to zero;

if the state counter value recorded by said processor is greater than a state threshold value, controls said periodic motion counter to increment a motion counter value, wherein the motion counter value is associated with a number of times the periodic motion of the object has occurred; and outputs the number of times the periodic motion of the object has occurred based on the motion counter value kept by the periodic motion counter;

whereby the periodic motion of the object may be measured regardless of the kind of periodic motion, including divergent movements of the object, including swinging, shaking, and rotating, and regardless of the orientation of the x-axis of the accelerometer about its y-axis.

11. The apparatus according to claim 10, wherein said processor:
inputs the axial acceleration and the radial acceleration respectively to the reverse process;
generates a sign-processed axial acceleration and a sign-processed radial acceleration, respectively based on results of the reverse process;
wherein the axial acceleration and the radial acceleration respectively serve as an input acceleration to the inverse process, and the reverse process includes:
calculating an average of a plural entries of the input accelerations received within a previous first time period; and
multiplying a latest one of the plural entries of the input accelerations by minus one if the inequality is satisfied by the average thus calculated;
wherein the inequality is one of the average is greater than zero and the average is smaller than zero; and
wherein the sign-processed axial acceleration and the sign-processed radial acceleration correspond to the axial acceleration and the radial acceleration for calculating the first included angle and the second included angle in step (B).

12. The apparatus according to claim 11
wherein said accelerometer further generates an orthogonal acceleration that represents a third component of the acceleration of the object in another direction that is orthogonal to both the axial direction and the radial direction; and
wherein said processor further:
inputs the orthogonal acceleration to the reverse process;
generates a sign-processed orthogonal acceleration based on a result of the reverse process, the orthogonal acceleration serving as the input acceleration to the reverse process; and
calculates a combined radial acceleration by subjecting the sign-processed radial acceleration and the sign-processed orthogonal acceleration to an addition equation, the combined radial acceleration thus calculated serving as the radial acceleration for calculating the first included angle and the second included angle.

13. The apparatus according to claim 12, wherein a magnitude of the combined radial acceleration equals a magnitude of the sign-processed radial acceleration plus a magnitude of the sign-processed orthogonal acceleration.

14. The apparatus according to claim 10:
wherein said accelerometer generates plural entries of the axial accelerations and plural entries of the radial accelerations within a previous second time period;
wherein said processor calculates a plurality of the first included angles and a plurality of the second included angles within the previous second time period based on the axial accelerations and the radial accelerations; and
wherein said processor performs a shifting process which includes:
calculating a first average of the first included angles and a second average of the second included angles;
calculating a difference by subtracting the first average from the second average; and
calculating a shifted first included angle by adding the difference to a latest one of the first included angles calculated within the previous second time period.

15. The apparatus according to claim 10:
wherein said accelerometer generates plural entries of the axial accelerations and plural entries of the radial accelerations within a previous third time period;
wherein said processor records a plurality of the state counter values within the previous third time period; and
wherein the state threshold value is calculated by multiplying an average of the state counter values thus recorded by a factor that ranges between 0 and 1.

16. The apparatus according to claim 10:
wherein said accelerometer generates plural entries of the axial accelerations and plural entries of the radial accelerations within a previous fourth time period;
wherein said processor calculates a plurality of the first included angles and a plurality of the second included angles within the previous fourth time period based on the axial accelerations and the radial accelerations; and
wherein said processor:
calculates an absolute difference between each set of the first included angle and the second included angle; and
controls said periodic motion counter to increment the motion counter value if a sum of the absolute differences calculated within the previous fourth time period is greater than a difference threshold value.

17. The apparatus according to claim 10:
wherein said accelerometer generates plural entries of the axial accelerations and plural entries of the radial accelerations within a previous fifth time period;
wherein said processor inputs each of a latest one of the axial accelerations and a latest one of the radial accelerations received within the previous fifth time period to a smoothing process;
wherein the smoothing process includes calculating an average of a respective one of the axial accelerations and the radial accelerations within the previous fifth time period, the average thus calculated serving as a corresponding one of the axial acceleration and the radial acceleration for calculating the first included angle and the second included angle.

18. The apparatus according to claim 10, wherein said processor is configured to multiply the motion counter value by two to serve as the number of times the periodic motion of the object has occurred.

19. A method for counting periodic motion of an object during sport activity, the method to be implemented by a processor included in a counter device, the counter device further including a processor, at least two accelerometers each attached to the object, a state counter, and a motion counter, the method comprising the acts of:
detecting accelerations associated with motion of the object by using the respective two accelerometers;
obtaining accelerations detected by the respective two accelerometers, where one of the accelerations serves as an axial acceleration while the other one of the accelerations serves as a radial acceleration;
performing at least one numerical operation upon the axial acceleration and the radial acceleration;
calculating a first included angle between a composite acceleration and the axial acceleration, and a second included angle between the composite acceleration and the radial acceleration, where the composite acceleration is a sum of the axial acceleration and the radial acceleration;

controlling the state counter to increment a state counter value if the second included angle is greater than the first included angle;

if the second included angle is not greater than the first included angle, recording the state counter value kept by the state counter, and resetting the state counter to zero;

determining whether the periodic motion has occurred one time based on the state counter values recorded within previous M seconds of repetition of the aforementioned steps and a sum of differences between the first includes angles and the second included angles calculated in the repetition of the aforementioned steps, a flow of the method going back to the step of obtaining accelerations when a result of the determination is negative;

when the result of the determination is affirmative, controlling the motion counter to increment a motion counter value kept thereby;

in response to receipt of a request, calculating a counting result of a number of times the periodic motion has occurred by multiplying the motion counter value by a predefined parameter associated with the sport activity; and outputting the counting result thus calculated;

whereby the periodic motion of the object may be measured regardless of the kind of periodic motion, including divergent movements of the object.

\* \* \* \* \*